(12) United States Patent
Weingarten

(10) Patent No.: US 11,076,818 B2
(45) Date of Patent: Aug. 3, 2021

(54) METHOD FOR OPERATING AN X-RAY DEVICE WITH AN ARTICULATED ARM, AND X-RAY DEVICE WITH AN ARTICULATED ARM

(71) Applicant: Siemens Healthcare GmbH, Erlangen (DE)

(72) Inventor: Markus Weingarten, Bamberg (DE)

(73) Assignee: Siemens Healthcare GmbH, Erlangen (DE)

( * ) Notice: Subject to any disclaimer, the term of this patent is extended or adjusted under 35 U.S.C. 154(b) by 231 days.

(21) Appl. No.: 15/998,682

(22) Filed: Aug. 15, 2018

(65) Prior Publication Data

US 2019/0053774 A1 Feb. 21, 2019

(30) Foreign Application Priority Data

Aug. 15, 2017 (EP) .................................... 17186236

(51) Int. Cl.
*A61B 6/00* (2006.01)
*A61B 6/10* (2006.01)
(Continued)

(52) U.S. Cl.
CPC ............ *A61B 6/102* (2013.01); *A61B 6/0487* (2020.08); *A61B 6/4429* (2013.01);
(Continued)

(58) Field of Classification Search
CPC .......... A61B 6/4405; A61B 6/461; A61B 6/54
See application file for complete search history.

(56) References Cited

U.S. PATENT DOCUMENTS

| 5,485,502 A * | 1/1996 | Hinton | .................... A61B 6/102 |
| | | | 250/363.01 |
| 8,570,373 B2 * | 10/2013 | Variyath | .................... G01S 5/02 |
| | | | 348/143 |

(Continued)

FOREIGN PATENT DOCUMENTS

| DE | 102008057142 A1 | 11/2009 |
| DE | 102008046348 A1 | 3/2010 |

(Continued)

OTHER PUBLICATIONS

European Search Report for corresponding Application No. 17186236. 0-1124, dated Feb. 15, 2018.

*Primary Examiner* — David P Porta
*Assistant Examiner* — Djura Malevic
(74) *Attorney, Agent, or Firm* — Lempia Summerfield Katz LLC

(57) ABSTRACT

A method for operating the X-ray device, which includes a detector, a radiation source, or a C-arm including the detector and the radiation source, and an articulated arm and a base. Initially, a starting position of the X-ray device is specified with respect to the detector, the radiation source, or the C-arm, and the articulated arm, and an end position of the X-ray device is specified at least with respect to the detector, the radiation source, or the C-arm. A plurality of paths that may be followed by the articulated arm and the detector, the radiation source, or the C-arm on movement from the starting position into the end position are automatically determined. One path of the plurality of paths for the movement of the X-ray device is selected, and the X-ray device is moved into the end position.

14 Claims, 1 Drawing Sheet

(51) Int. Cl.
*G05B 19/4061* (2006.01)
*B25J 9/16* (2006.01)
*A61B 6/04* (2006.01)

(52) U.S. Cl.
CPC .......... *A61B 6/4441* (2013.01); *A61B 6/4476* (2013.01); *A61B 6/54* (2013.01); *B25J 9/1664* (2013.01); *B25J 9/1666* (2013.01); *G05B 19/4061* (2013.01); *A61B 6/466* (2013.01); *A61B 6/467* (2013.01); *G05B 2219/40476* (2013.01); *G05B 2219/40519* (2013.01); *G05B 2219/45169* (2013.01)

(56) References Cited

U.S. PATENT DOCUMENTS

| | | | |
|---|---|---|---|
| 10,265,035 B2* | 4/2019 | Fehre | G16H 30/20 |
| 10,292,005 B2* | 5/2019 | Jordan | H04W 4/02 |
| 2007/0018820 A1* | 1/2007 | Chand | G01C 21/206 |
| | | | 340/572.1 |
| 2009/0097612 A1 | 4/2009 | Rauch | |
| 2009/0271035 A1* | 10/2009 | Lurz | A61B 6/4458 |
| | | | 700/245 |
| 2014/0274031 A1* | 9/2014 | Menendez | H04W 52/0209 |
| | | | 455/426.1 |
| 2015/0134145 A1* | 5/2015 | Lee | G05D 1/0265 |
| | | | 701/2 |
| 2016/0242715 A1* | 8/2016 | Schmidt | A61B 6/54 |
| 2017/0347979 A1 | 12/2017 | Fehre et al. | |

FOREIGN PATENT DOCUMENTS

| | | |
|---|---|---|
| DE | 102016201701 A1 | 8/2016 |
| DE | 102016209576 A1 | 12/2017 |
| WO | WO2011075232 A1 | 6/2011 |

* cited by examiner

METHOD FOR OPERATING AN X-RAY DEVICE WITH AN ARTICULATED ARM, AND X-RAY DEVICE WITH AN ARTICULATED ARM

This application claims the benefit of, filed on Aug. 15, 2017, which is hereby incorporated by reference in its entirety.

BACKGROUND

The present embodiments relate to operating an X-ray device.

In the following, for simplification, the present embodiments are described with reference to a C-arm X-ray device, without this intending to restrict the invention to use with C-arm X-ray devices. Instead, the present embodiments may also be used with X-ray devices with which, instead of a C-arm with a detector and radiation source, only a detector or a radiation source is arranged on an articulated arm.

A C-arm X-ray device usually has a base mounted rotatably on the ground. Typically, an articulated arm that may be moved in all spatial directions is attached to the base at a proximal end. A C-arm is fastened in a movable manner to the distal end of the articulated arm. At one end of the C-arm, there is an X-ray source, and at the other end of the C-arm, there is a, generally plate-shaped, detector.

C-arm X-ray devices are used to transilluminate objects. Objects may be not only patients, but also workpieces such as, for example, turbine blades. There is frequently a requirement to produce 3D images of the transilluminated objects. To this end, the C-arm adopts very many different positions with respect to the object. It may also be necessary to monitor dynamic processes, such as, for example, the positioning of a catheter, with the C-arm X-ray device. In this case, the C-arm has to be tracked accordingly. All these movements of the C-arm X-ray device are enabled in that the C-arm X-ray device is provided with a plurality of axes that are controlled accordingly. Such a C-arm X-ray device frequently has six, fewer, or more axes. These axes are to be moved in a complex way during a moving operation. It is not rare for such a C-arm X-ray device to be overdetermined in that a specific position of the C-arm may be reached from an original starting position via a plurality of different movement trajectories or paths. Typically, the system itself calculates a path for traveling from a starting position to a prespecified end position.

C-arm X-ray devices frequently have dimensions of several meters in length, breadth, and height. Accordingly, C-arm X-ray devices also have a relatively high weight. Therefore, automated movements of the C-arm X-ray device may present a significant risk to people working with the C-arm X-ray device or in the environment thereof. Although the people involved frequently know the end position of a C-arm, the people do not know the path or paths followed by the individual components of the C-arm X-ray device connected to the joints during the respective movement. Therefore, movements of the C-arm X-ray device repeatedly result in hazards to the people involved.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a risk to people and objects from a C-arm X-ray device on movement thereof is reduced.

According to one or more of the present embodiments, a method is provided for operating a C-arm X-ray device including a C-arm with a detector and a radiation source, an articulated arm, and at least one (e.g., two) base. Operation of the C-arm X-ray device typically takes place in a laboratory or an operating theater.

Initially, this entails specification of a starting position of the C-arm X-ray device with respect to the C-arm and the articulated arm. This specification of the starting position may be performed automatically by a suitable sensor system. Herein, the starting position includes, for example, the position of the individual elements of the C-arm X-ray device with respect to one another and possibly also the position of the C-arm X-ray device in the surrounding area. In the present case, there is particular interest in determining or specifying this starting position with respect to the C-arm and the articulated arm of the C-arm X-ray device. Therefore, importance is attached to the location of the C-arm and the articulated arm at the beginning of a movement (e.g., the starting position the C-arm and the articulated arm adopt or the C-arm X-ray device adopts).

One or more of the present embodiments also entail the specification of an end position of the C-arm X-ray device at least with respect to the C-arm. The C-arm, including the detector and radiation source, moves into a predetermined position (e.g., relative to an object). At the end of this movement, the C-arm adopts the corresponding end position. This end position may be specified automatically or manually.

This also entails movement of the C-arm X-ray device from the starting position into the end position. Since, typically, the articulated arm and the C-arm on the articulated arm are movable, an appropriate number of axes are controlled or moved during the movement of the C-arm X-ray device. There are a plurality of routes or paths on which the C-arm or the C-arm X-ray device may reach the end position.

According to one or more of the present embodiments, there is now an automatic ascertainment of a plurality of paths that may be followed by the arm and the C-arm on movement from the starting position into the end position. Therefore, for example, a plurality of complete paths on which the C-arm and the articulated arm may move in order to reach the end position are calculated. In one embodiment, a path is a route traversed, for example, by the center of gravity of a component of the C-arm X-ray device (e.g., C-arm or articulated arm) from the initial starting position to the end position of the C-arm X-ray device. However, the path may represent a complex geometric entity on which a plurality of components of the C-arm X-ray device move. In one embodiment, the path represents the spatial area within which the C-arm and the articulated arm move. In a simpler embodiment, the path is a 2D projection of this area.

One path of the plurality of paths for the movement of the C-arm X-ray device is selected (e.g., manually or automatically). In one embodiment, a user of the C-arm X-ray device, for example, selects one path of the plurality of paths. In some circumstances, the person making the selection takes account of other people or objects in the environment of the C-arm X-ray device in the selection. This enables it to be provided that the moving C-arm X-ray device presents less risk to the people and objects in the environment. It is, for example, possible for a path to be selected with which all collisions are avoided.

In one development, the end position of the C-arm X-ray device is also specified with respect to the articulated arm and/or the base. Therefore, the end position of the C-arm X-ray device is to be specified, not only with respect to the C-arm, but also with respect to one or more other components of the C-arm X-ray device (e.g., the articulated arm or the base). This may achieve a very specific end position of the C-arm X-ray device.

The starting position of the C-arm X-ray device may also be specified with respect to the base. In addition to the relative position of the base with respect to the articulated arm, a relative position of the base with respect to an area in which the C-arm X-ray device is installed (e.g., an operating theater) may be taken into account. All moving main components of the C-arm X-ray device are taken into account with the starting position.

In one embodiment, on the ascertainment of the plurality of paths, an object in the environment of the C-arm X-ray device is automatically taken into account. Therefore, if, for example, an object different from the C-arm X-ray device (e.g., a scrub nurse or anesthesia machine) is located in the immediate vicinity of the C-arm X-ray device, the object is detectable by a suitable sensor system. If the object restricts the collision-free movement area of the C-arm X-ray device, this should be taken into account in the ascertainment of the plurality of paths. The device may then only ascertain or suggest paths that do not result in a collision. The object may be detected by photoelectric barriers, ultrasound sensors, cameras, and the like.

In one embodiment, the plurality of paths is depicted graphically for selection. For example, therefore, a user interface with a screen depicting the plurality of paths graphically, for example, with respect to the C-arm X-ray device or detected objects may be provided. The different paths may optionally be depicted in different colors with respect to one another. Optionally, the user may select a respective path by touch (e.g., in the case of a touchscreen) or by keyboard input, voice, gestures, or another method of operation.

Therefore, the selection of the path for the movement of the C-arm X-ray device may be performed manually. This enables it to be provided that a fixed path is not automatically used for the movement. Instead, the user (e.g., the operator) may decide which path the C-arm X-ray device is to use for movement. This enables account to be taken of additional conditions, such as, for example, the position of the people in the area, the equipment in the area, or the operator's preferences.

It may also be provided that the selection of the path for the movement of the C-arm X-ray device takes place automatically in accordance with a learning process performed by the C-arm X-ray device. This provides that the C-arm X-ray device automatically learns previous manual selection operations. Therefore, if, for example, heart-valve surgery is to be performed several times, the surgeon and assistants are always in the same places. The same applies, for example, to anesthesia equipment. Therefore, the C-arm X-ray device may select one of many possible paths as a standard path, so that this is, for example, highlighted graphically on a display. The user of the C-arm X-ray device may then use a simple confirmation (e.g., by a button) to confirm the automatically selected path or activate the corresponding movement.

In a further embodiment, during the selection, one of the paths is automatically preselected, and correction options for the correction of the automatic path are provided on an operator interface of the C-arm X-ray device. For example, the C-arm X-ray device suggests a standard path, and this standard path may now be corrected. This provides the user with numerous options for influencing the path. The user may simultaneously be suggested a path that the machine considers to be optimal and that may only need to be modified with respect to obstacles.

In one embodiment, the automatic ascertainment of a plurality of paths is updated continuously. This may be advantageous for various reasons. The C-arm X-ray device may be manually displaced following a last ascertainment of the paths. This makes it necessary to ascertain the current starting position, and also the plurality of paths, once again. The environment C-arm X-ray device may have changed during operation. For example, an auxiliary table may be displaced, or a person may have moved in the area. This may necessitate the calculation of completely new paths. If this automatic ascertainment of the paths is performed continuously or consecutively, a plurality of current paths is available at all times.

In one embodiment, a C-arm X-ray device includes a C-arm, with a detector and radiation source, and an articulated arm. The C-arm is arranged on a distal end of the articulated arm. The C-arm X-ray device also includes a base, to which a proximal end of the articulated arm is attached, and a movement device, by which the C-arm X-ray device may be moved from a starting position specified with respect to the C-arm and the articulated arm may be moved into an end position specified with respect to the C-arm. The C-arm X-ray device includes a computer for the automatic ascertainment of a plurality of paths that may be followed by the articulated arm and the C-arm on movement from the starting position into the end position. The C-arm X-ray device includes a selector for the selection of one path of the plurality of paths for the movement of the C-arm X-ray device.

The advantages and possible developments described above in connection with the method also apply analogously to the C-arm X-ray device. The corresponding devices of the C-arm X-ray device have the respective functions described as method features.

DETAILED DESCRIPTION

Exemplary embodiments are described in more detail below. The individual features may be implemented not only in the described feature combinations, but also on their own or in other technically advisable combinations.

Figure 1:
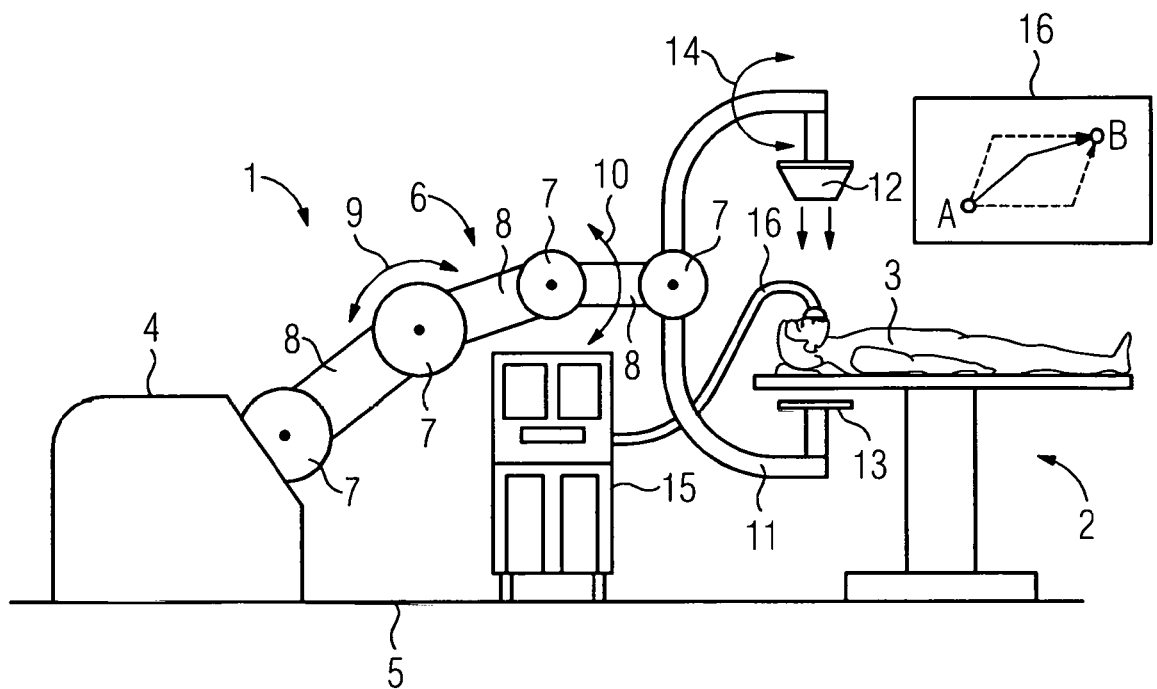
FIG. 1 shows a schematic view of one embodiment of a C-arm X-ray device during operation in an operating theater.

FIG. 1 is a schematic view of one embodiment of a medical system with a C-arm X-ray device 1 and a patient couch 2 on which a patient 3 is located. The C-arm X-ray device 1 includes a base 4 that is, for example, attached rotatably on the floor 5. The C-arm X-ray device 1 includes an articulated arm 6 mounted pivotably and/or rotatably on the base 4 by a proximal end. The articulated arm 6 includes, for example, a plurality of joints 7 and in each case between two of these joints 7 a respective arm section 8. The number of joints 7 or arm sections 8 may be chosen freely. The articulated arm 6 permits movements 9, 10 in different spatial directions. For example, the entire C-arm X-ray device 1 has six motion axes in order to carry out correspondingly complex movements.

A C-arm 11 is arranged on the distal end of the articulated arm 6. There is an X-ray source 12 on one end of the C-arm 11 and a detector 13 on another end. The C-arm 11 may, for example, be subject to angulation 14.

In addition, in the area (e.g., operating theater), there is an anesthesia machine or ventilator 15 in the immediate vicinity of the C-arm X-ray device 1 or the patient couch 2 with the patient 3. A hose 17 leads from the ventilator 15 to the patient 3.

The ventilator 15 and the hose 17 are representative of all possible objects that may restrict the movement of the C-arm X-ray device 1. Any object in the vicinity of the C-arm X-ray device 1 restricts the area in which the device may move without collision. Such objects include other devices or supply systems (e.g., including cables and hoses) and people.

An operator interface 16 is arranged on the C-arm X-ray device 1 or in the area (e.g., operating theater). This operator interface 16 provides information on, for example, the movement possibilities for the C-arm X-ray device 1.

In the present case, the C-arm X-ray device 1 is to move from a first point A to a second point B. Herein, in the simplest case, for example, only the center point between the X-ray source 12 and the detector 13 is considered to be the definitive point. Therefore, this point is to migrate from point A to point B. The system now suggests, for example, three paths as to how point B may be reached starting from point A, as shown on the operator interface 16 (e.g., touch monitor) in FIG. 1. In one embodiment, only two paths or even more than three paths may be suggested. The operator chooses one path of the plurality of paths by making a corresponding entry in the operator interface 16. For example, the operator taps one of the paths shown. This may select not only the desired path, but may also activate the C-arm X-ray device 1 for the corresponding movement.

In selecting the path, the user or operator takes account of the objects or people in the environment of the C-arm X-ray device 1. For example, collision-free movement may take place from a starting position A of the C-arm X-ray device 1 into an end position B.

Figure 2:
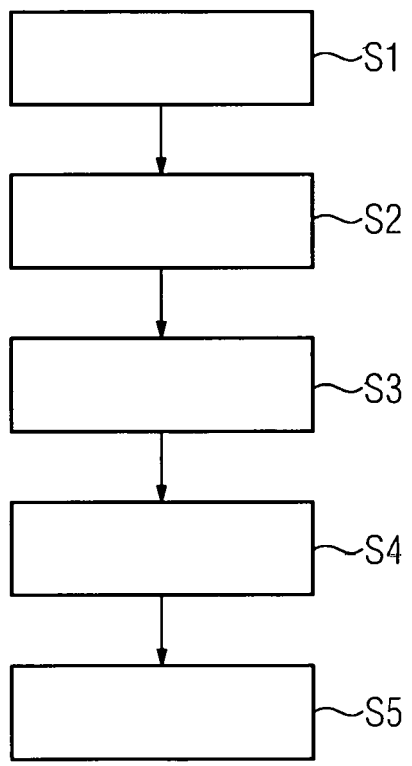
FIG. 2 shows a diagram illustrating the course of a method according to an embodiment.

FIG. 2 may be used to explain the procedure for operating a C-arm X-ray device in more detail. Initially, in act S1, a starting position of the C-arm X-ray device 1 is specified. For example, the starting position takes account not only of the C-arm 11, but also the articulated arm 6. Due to the large number of axes, the articulated arm 6 executes complex movements and, due to large physical extensions, also is to be taken into account during the movement of the C-arm X-ray device 1 in addition to the actual C-arm 11. The specification of the starting position is performed automatically by the sensor system of the C-arm X-ray device 1 since the joint settings of the joints 7 are detected automatically. The dimensions of the arm sections 8, the joints 7, and the base 4 and the C-arm 11 then enable the respective starting position of the C-arm X-ray device 1 to be ascertained or specified exactly.

In a subsequent act S5, the end position of the C-arm X-ray device 1 is specified at least with respect to the C-arm 11. The C-arm 11 is to be brought into a specific position in order to be available there for a desired X-ray recording. The shape adopted by the articulated arm 6 is of secondary importance for this setting of the C-arm 11. For a safe movement of the C-arm X-ray device 1 from a starting position A to an end position B, however, the movement and shape of the articulated arm 6 is also of decisive importance.

In order to establish how the C-arm X-ray device 1 may be moved into the desired end position at least with respect to the C-arm 11, according to act S3, a plurality of paths that the articulated arm 6 and the C-arm 11 may follow on movement from the starting position A into the end position B is ascertained automatically. In one embodiment, this plurality of paths is depicted graphically on a monitor or another operator interface 16. In a subsequent act S4, one path of the plurality of paths ascertained for the movement of the C-arm X-ray device 1 is selected. For this, for example, the desired path is tapped on the operator interface 16. For example, the path chosen is a path that guarantees that the C-arm X-ray device 1 does not collide with an object or a person while moving.

According to act S5, the C-arm X-ray device 1 moves along the selected path. This movement is, for example, activated by manual confirmation or selection of one path of the plurality of paths.

In one embodiment, on the user interface 16, a path is not only depicted as a line (e.g., the center point between the X-ray source 12 and the detector 13), but as an area of space traversed or passed by the C-arm X-ray device 1 during movement. As a result, each path becomes to a two-dimensional or three-dimensional entity. Hence, a user has a better overview of the regions or areas required by the C-arm X-ray device 1 for movements. As a result, the people and/or objects in the region of the C-arm X-ray device 1 may be acquired and displayed graphically on the user interface 16. However, in one embodiment, the only paths suggested for the movement are the paths that avoid collision with objects or people.

Optionally, the system also learns to suggest specific paths as standard paths. For example, it the paths may be personalized. For example, if a specific operator always has the anesthesia machinery, for example, on the left side of the patient couch, this may be taken into account when ascertaining the plurality of paths or when specifying a standard path.

The method described may be embodied as dynamic. If, for example, the doctor pulls the patient couch 2 back, another trajectory or another path that is also to be displayed instantaneously on the user interface 16 is enabled for the movement of the C-arm X-ray device 1. Therefore, the automatic ascertainment of a plurality of paths may be performed continuously.

The method for the operation of a C-arm X-ray device may be used not only to move the C-arm X-ray device from one examination position into another examination position. The method may also be used, for example, to move the C-arm X-ray device from a parked position, in which the C-arm 11 is, for example, located on the ceiling, into an examination position. The current situation is to be accounted for in order avoid collisions.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating an X-ray device comprising a detector, a radiation source, or a C-arm with the detector and the radiation source, and an articulated arm and a base, the method comprising:
specifying a starting position of the X-ray device with respect to the C-arm, the detector, or the radiation source, and with respect to the articulated arm;
specifying an end position of the X-ray device at least with respect to the C-arm, the detector, or the radiation source;
moving the X-ray device from the starting position into the end position;
automatically ascertaining a plurality of paths that are followable by the articulated arm and the C-arm, the detector, or the radiation source on movement from the starting position into the end position;
graphically depicting the plurality of paths for selection; and
selecting one path of the plurality of paths for the movement of the X-ray device, wherein selecting the one path of the plurality of paths for the movement of the X-ray device is based on manual selection of the one path.

2. The method of claim 1, wherein specifying the end position of the X-ray device comprises specifying the end position of the X-ray device with respect to the articulated arm, the base, or the articulated arm and the base.

3. The method of claim 1, wherein specifying the starting position of the X-ray device comprises specifying the starting position of the X-ray device with respect to the base.

4. The method of claim 1, wherein automatically ascertaining the plurality of paths comprises automatically taking account of an object in an environment of the X-ray device.

5. The method of claim 1, wherein selecting one path of the plurality of paths for the movement of the X-ray device comprises selecting the one path automatically in accordance with a learning process performed by the X-ray device.

6. The method of claim 1, wherein selecting one path of the plurality of paths comprises:
automatically preselecting a path of the plurality of paths; and
providing correction options for correction of the automatically preselected path on an operator interface of the X-ray device.

7. The method of claim 1, wherein the automatic ascertainment of the plurality of paths is updated continuously.

8. An X-ray device comprising:
a detector, a radiation source, or a C-arm including the detector and the radiation source;
an articulated arm, wherein the C-arm, the detector, or the radiation source is arranged on a distal end of the articulated arm;
a base to which a proximal end of the articulated arm is attached;
a movement device by which the X-ray device is movable from a starting position specified with respect to the C-arm, the detector, or the radiation source, and with respect to the articulated arm into an end position specified with respect to the C-arm, the detector, or the radiation source;
a computer configured for automatic ascertainment of a plurality of paths that are folllowable by the articulated arm and the C-arm, the detector, or the radiation source on movement from the starting position into the end position;
a display configured to graphically depict the plurality of paths for selection; and
a selector configured for selection of one path of the plurality of paths for the movement of the X-ray device, wherein the selection of the one path of the plurality of paths for the movement of the X-ray device is based on manual selection of the one path.

9. The X-ray device of claim 8, wherein specification of the end position of the X-ray device comprises specification of the end position of the X-ray device with respect to the articulated arm, the base, or the articulated arm and the base.

10. The X-ray device of claim 8, wherein specification of the starting position of the X-ray device comprises specification of the starting position of the X-ray device with respect to the base.

11. The X-ray device of claim 8, wherein the automatic ascertainment of the plurality of paths comprises automatic taking account of an object in an environment of the X-ray device.

12. The X-ray device of claim 8, wherein the selection of the one path of the plurality of paths for the movement of the X-ray device comprises selection of the one path automatically in accordance with a learning process performed by the X-ray device.

13. The X-ray device of claim 8, wherein the selection of the one path of the plurality of paths comprises:
automatic preselection of a path of the plurality of paths; and
provision of correction options for correction of the automatically preselected path on an operator interface of the X-ray device.

14. The X-ray device of claim 8, wherein the automatic ascertainment of the plurality of paths is updated continuously.

* * * * *